(12) United States Patent
Yoneda

(10) Patent No.: US 6,837,595 B2
(45) Date of Patent: Jan. 4, 2005

(54) SURFACE INSPECTING ILLUMINATION DEVICE AND SURFACE INSPECTING APPARATUS

(75) Inventor: Kenji Yoneda, Kyoto (JP)

(73) Assignee: CCS Co., Ltd., Kyoto (JP)

( * ) Notice: Subject to any disclaimer, the term of this patent is extended or adjusted under 35 U.S.C. 154(b) by 229 days.

(21) Appl. No.: 10/110,275

(22) PCT Filed: Aug. 2, 2001

(86) PCT No.: PCT/JP01/06678

§ 371 (c)(1),
(2), (4) Date: Apr. 10, 2002

(87) PCT Pub. No.: WO02/16918

PCT Pub. Date: Feb. 28, 2002

(65) Prior Publication Data

US 2002/0136009 A1 Sep. 26, 2002

(30) Foreign Application Priority Data

Aug. 22, 2000 (JP) .................................... P2000-251595
Nov. 30, 2000 (JP) .................................... P2000-366089

(51) Int. Cl.⁷ ............................. F21V 19/02; F21V 5/00
(52) U.S. Cl. ....................... 362/249; 362/138; 362/238; 362/244
(58) Field of Search ................................ 362/249, 235, 362/800, 236, 237, 238, 240, 244–246, 252, 138, 139

(56) References Cited

U.S. PATENT DOCUMENTS 5,838,247 A * 11/1998 Bladowski ............. 340/815.45
6,161,941 A * 12/2000 Tait et al. .................... 362/249
6,450,664 B1 * 9/2002 Kelly ........................... 362/249

FOREIGN PATENT DOCUMENTS

| JP | 6-72046 | * | 3/1994 | .......... G01B/11/24 |
| JP | 6-72046 U | | 10/1994 | |
| JP | 8-254500 A | | 10/1996 | |
| JP | 9-21699 A | | 1/1997 | |
| JP | 9-96610 S | | 4/1997 | |

* cited by examiner

Primary Examiner—Alan Cariaso
Assistant Examiner—Mark Tsidulko
(74) Attorney, Agent, or Firm—Banner & Witcoff Ltd.

(57) ABSTRACT

In order to improve the lighting efficiency without incurring the upsizing of the system, a rise in price or the like, a lighting system for surface inspection to be suitably used in pattern inspection or the like of printed boards is provided wherein: a pair of light-emitting members are provided for lighting a given surface region of a subject for inspection obliquely from an upper forward side and an upper rearward side; and a second light-emitting member capable of lighting from just above through a half mirror is added to the pair of light-emitting members to enhance the lighting luminous intensity, each of the pair of light-emitting members including a plurality of LEDs arranged lengthwise and crosswise, and cylindrical lenses disposed correspondingly to respective columns of the LEDs.

20 Claims, 13 Drawing Sheets

SURFACE INSPECTING ILLUMINATION DEVICE AND SURFACE INSPECTING APPARATUS

CROSS REFERENCE TO RELATED APPLICATIONS

This is a U.S. National Phase Application under 35 U.S.C. § 371 and applicant herewith claims the benefit of priority of PCT/JP01/06678 filed Aug. 2, 2001, which was published Under PCT Article 21(2) in English, which claims priority to Japanese Application Nos. P2000-251595, filed Aug. 22, 2000 and P2000-366089, filed Nov. 30, 2000, the entire contents of which are incorporated herein by reference.

TECHNICAL FIELD

The present invention relates to a lighting system for surface inspection and a surface inspection unit, which are suitably used in pattern inspection or the like of printed boards.

BACKGROUND ART

Conventionally, in pattern inspection or the like of printed boards, there is a case where a method is employed which is adapted to inspect a board not entirely at a time but on a region-by-region basis, each region having a constant width extending laterally of the board, though whether or not to employ this method depends upon the sizes of boards. Specifically, a board being fed in on direction is exposed to band-like lighting along a line perpendicularly intersecting the feeding direction, and the images of flaws and the like present in an illuminated portion of the board are picked up one by one.

One known lighting system used for this type of application comprises a pair of elongate rectangular light-emitting members disposed to form a flared shape widening toward a board, the light-emitting members being adapted to light the region having a constant width to be illuminated obliquely from an upper forward side and an upper rearward side.

By the way, demand is growing for a higher board feeding speed with a view to, for example, shortening the inspection time to meet increasing volume production of products or the like and, hence, the lighting luminous intensity also needs to be enhanced with increasing feeding speed.

However, simply enhancing the luminous intensity of light emission itself is not preferable because it incurs upsizing of the lighting system and an increase in power consumption. Use of a lens for concentrating light emitted from the light-emitting members is easily conceivable. However, since each light-emitting member itself comprises a surface-emitting type light-emitting member having a certain width, the method of simply concentrating light requires a lens having a larger diameter, which may also incur upsizing of the lighting system and a rise in price.

DISCLOSURE OF INVENTION

Accordingly, a chief object of the present invention is to provide a lighting system for surface inspection and a surface inspection unit, which make it possible to improve the lighting efficiency without incurring upsizing of the system, a rise in price and the like, wherein a pair of light-emitting members for lighting a given surface region of a subject for inspection obliquely from an upper forward side and an upper rearward side comprise a plurality of LEDs arranged lengthwise and crosswise, and cylindrical lenses disposed correspondingly to respective columns of the LEDs, the positional relation between each of the LED columns and a corresponding one of the cylindrical lenses is made capable of concentrating light.

That is, a lighting system for surface inspection according to the present invention comprises: a pair of light-emitting members disposed to form a flared shape widening toward a subject for inspection in side view; a half mirror disposed on an opposite side from the subject for inspection about the light-emitting members; a second light-emitting member disposed on the opposite side from the subject for inspection about the light-emitting members such that light emitted from the second light-emitting member is reflected by the half mirror and then passes through a clearance defined between the pair of light-emitting members, the pair of light-emitting members each comprising a plurality of LEDs arranged in a matrix fashion on a side thereof facing the subject for inspection; and light-concentrating cylindrical lenses disposed correspondingly to respective columns of the LEDs, wherein the positional relation between each of the LED columns and a corresponding one of the cylindrical lenses is established such that light emitted from LEDs belonging to each LED column is concentrated onto a given surface region of the subject for inspection.

The lighting system thus constructed is capable of concentrating light emitted from the light-emitting members onto a given surface region of a subject for inspection through the cylindrical lenses and hence makes it possible to improve the lighting luminous intensity efficiently. Further, since there are provided plural columns of LEDs, correspondingly to which respective cylindrical lenses are disposed, it is possible to use an inexpensive cylindrical lens having a small diameter for each of the cylindrical lenses as well as to concentrate light by merely establishing a positional relation between each LED column and a corresponding one of the cylindrical lenses, whereby the downsizing of the system and the lowering of the price can be promoted with no heavy manufacturing burden.

BEST MODE FOR CARRYING OUT THE INVENTION

First Embodiment

Hereinafter, the first embodiment of the present invention will be described with reference to FIGS. 1 to 4.

Figure 1:
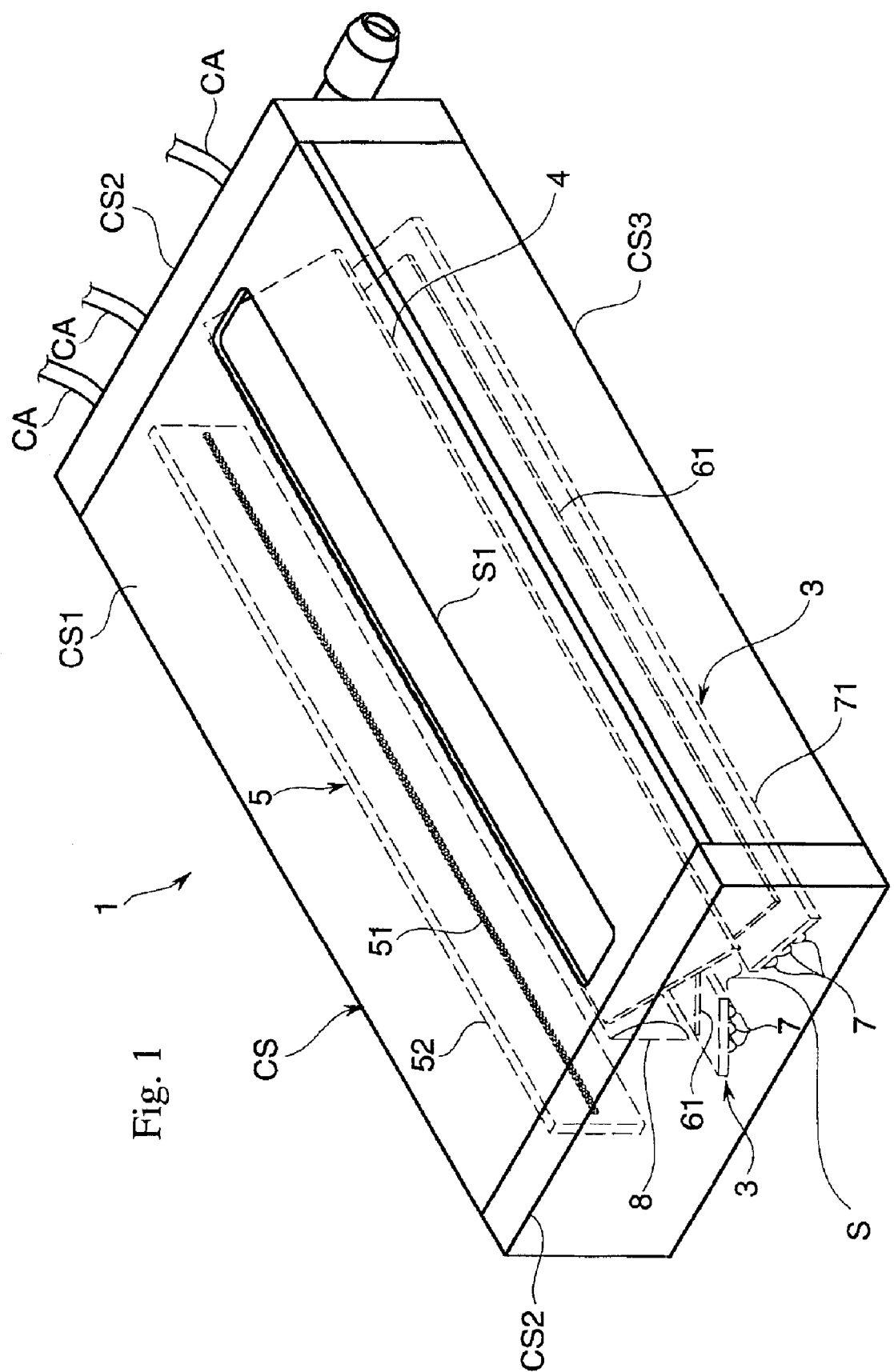
FIG. 1 is a general perspective view showing a lighting system for surface inspection in a first embodiment of the present invention.
Figure 2:
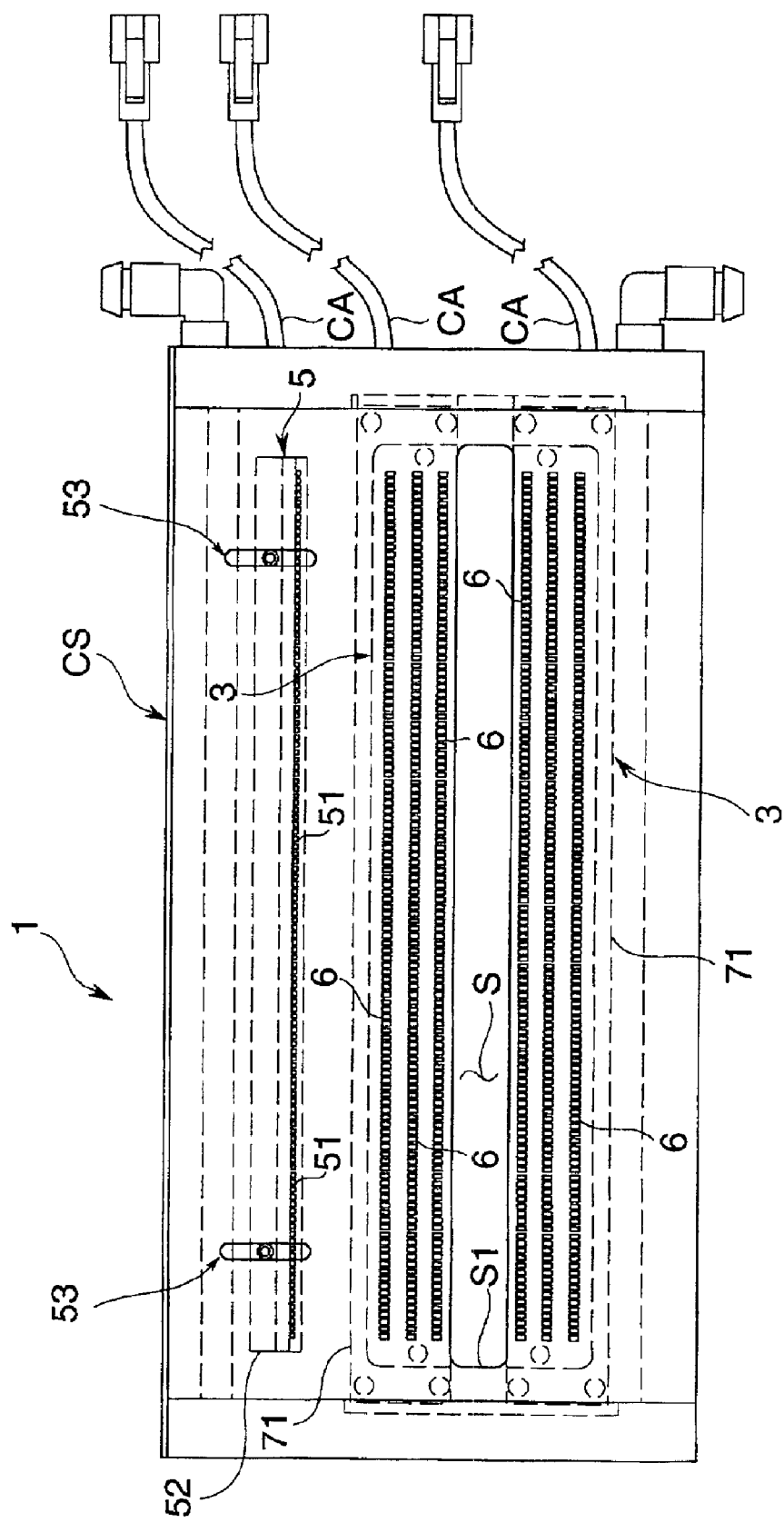
FIG. 2 is a plan view of the lighting system for surface inspection in the same embodiment.
Figure 3:
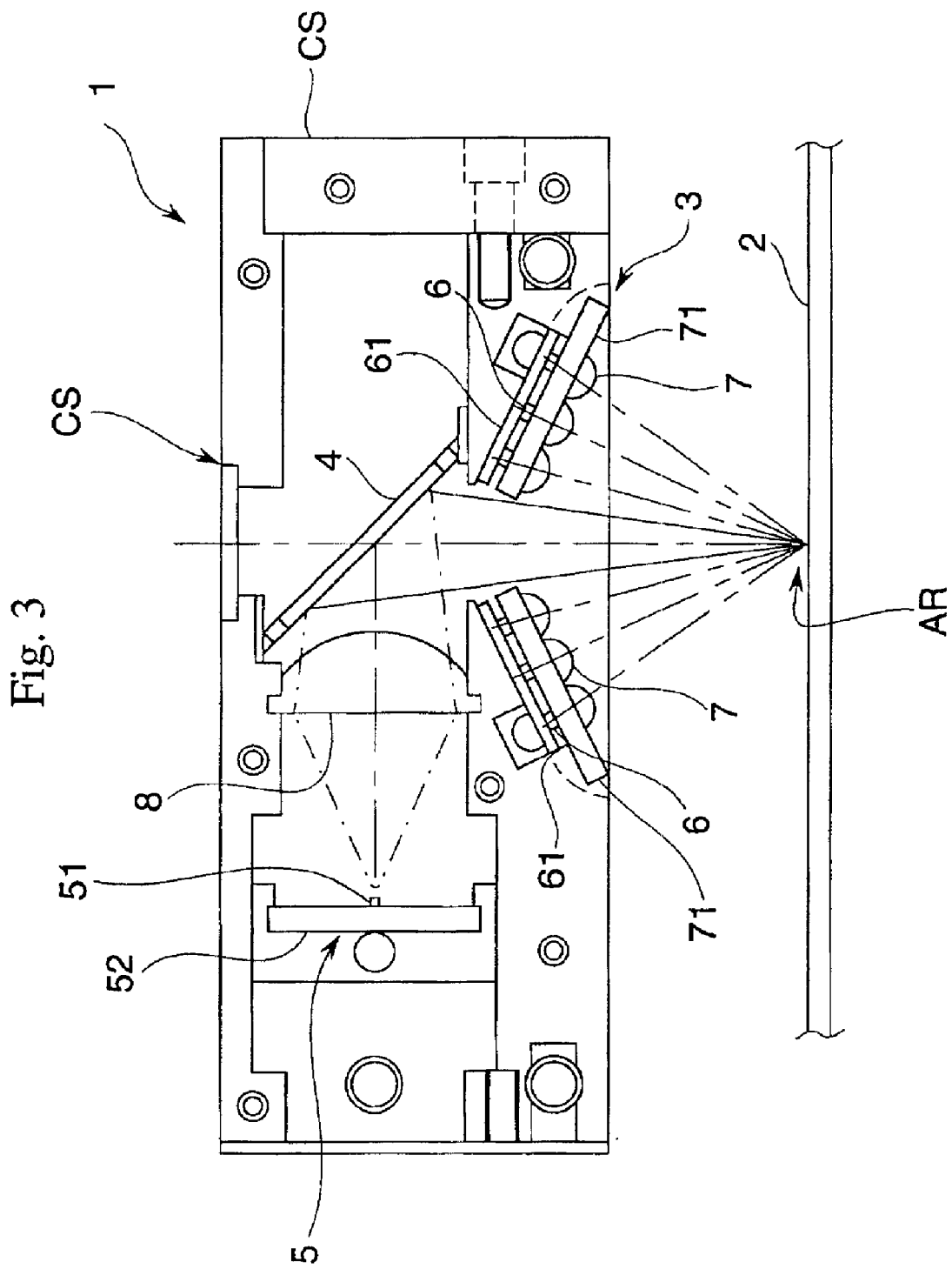
FIG. 3 is a side view showing the internal structure of the lighting system for surface inspection in the same embodiment.

Lighting system 1 for surface inspection shown in FIGS. 1 to 3 is adapted for inspection of surface unevenness or the like of a subject 2 for inspection (a printed board for example) and comprises a casing CS shaped into a rectangular parallelepiped with its one side open, a pair of light-emitting members 3 disposed within the casing CS, a second light-emitting member 5, and a half mirror 4. The lighting system 1 is disposed so that its open side faces the subject 2 while its longitudinal direction perpendicularly intersects the feeding direction of the subject 2.

Referring specifically to each part, the casing CS comprises a top plate CS1 and fore and rear plates CS3 laid crosswise as sandwiched between side plates CS2, the top plate CS1 defining a longitudinally extending rectangular through-window S1 in a portion thereof just above a clearance S defined between the light-emitting members 3 to be described later. In FIG. 1, reference character CA denotes a cable for supplying electric power to the pair of light-emitting members 3 and the second light-emitting member 5.

Figure 4:
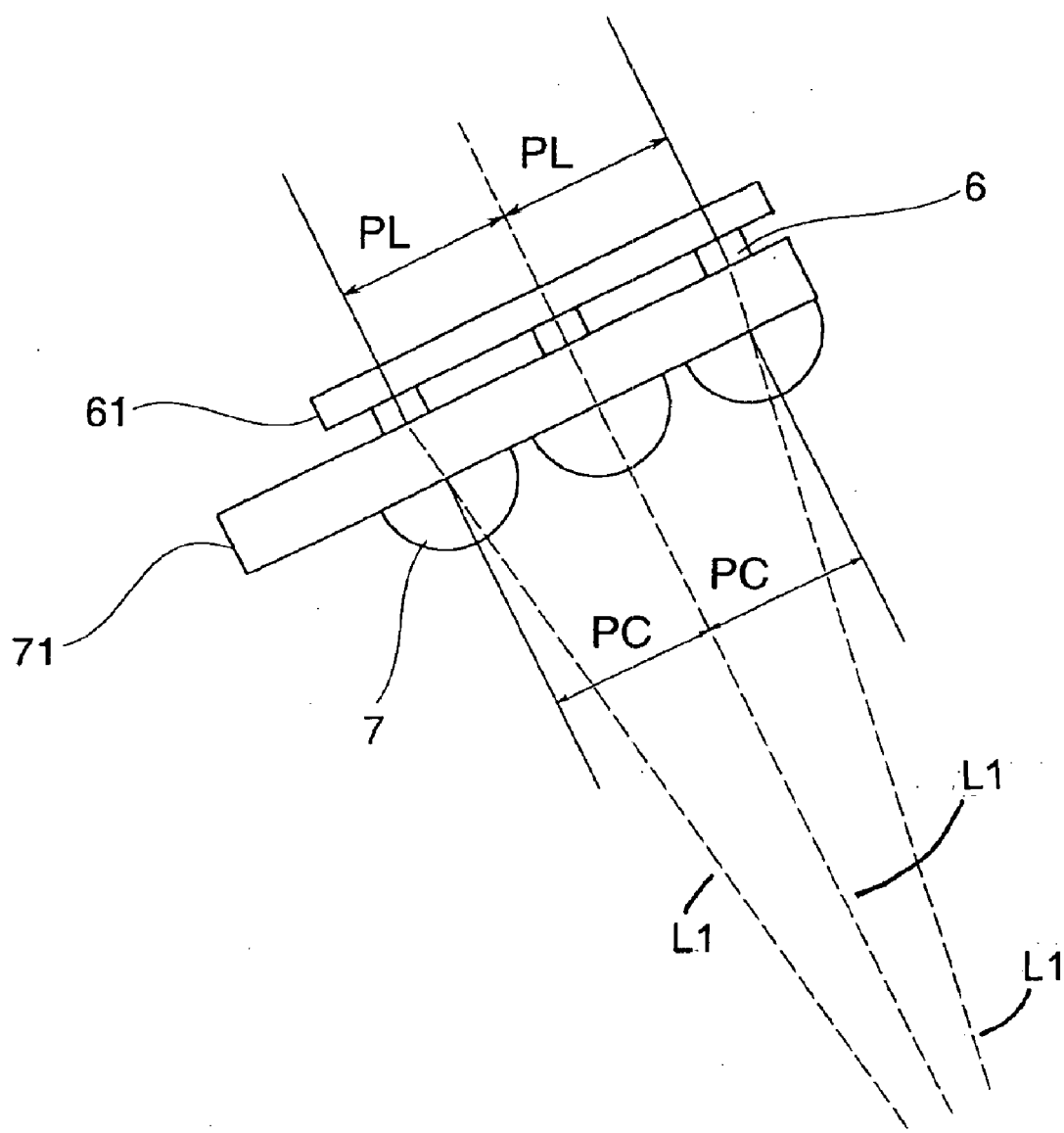
FIG. 4 is a detail view showing a partial structure of the lighting system for surface inspection in the same embodiment.

The light-emitting members 3 each comprise a plurality of chip-type LEDs 6, an LED support plate 61 supporting these LEDs 6, a plurality of cylindrical lenses 7, and a lens support plate 71 supporting these cylindrical lenses 7. The LED support plate 61 is a rectangular printed board extending along the longitudinal direction and having a side facing the subject 2 on which the LEDs 6 are arranged into a matrix extending lengthwise and crosswise, that is, arranged in columns extending in the same direction as the longitudinal direction and in rows extending in a direction perpendicularly intersecting the longitudinal direction. The lens support plate 71 is a transparent glass plate shaped substantially the same as the LED support plate 61 and disposed parallel with the subject 2—facing side of the LED support plate 71(sic). The cylindrical lenses 7 are each formed of a transparent resin such as an acrylic resin and shaped into a longitudinally-divided cylinder. The plural cylindrical lenses 7 are bonded to the subject 2—facing side of the lens support plate 71 so that each lens corresponds to a respective one of the columns of LEDs 6. More specifically, as shown in FIG. 4, pitch PL between adjacent columns of LEDs 6 and pitch PC between adjacent ones of the cylindrical lenses are established so that lines L1 each linking the luminescence center of an LED belonging to each column to the center of a corresponding cylindrical lens 7 are concentrated toward a given region of the subject 2. In the case of this embodiment, pitch PC is smaller than pitch PL.

Figure 9:
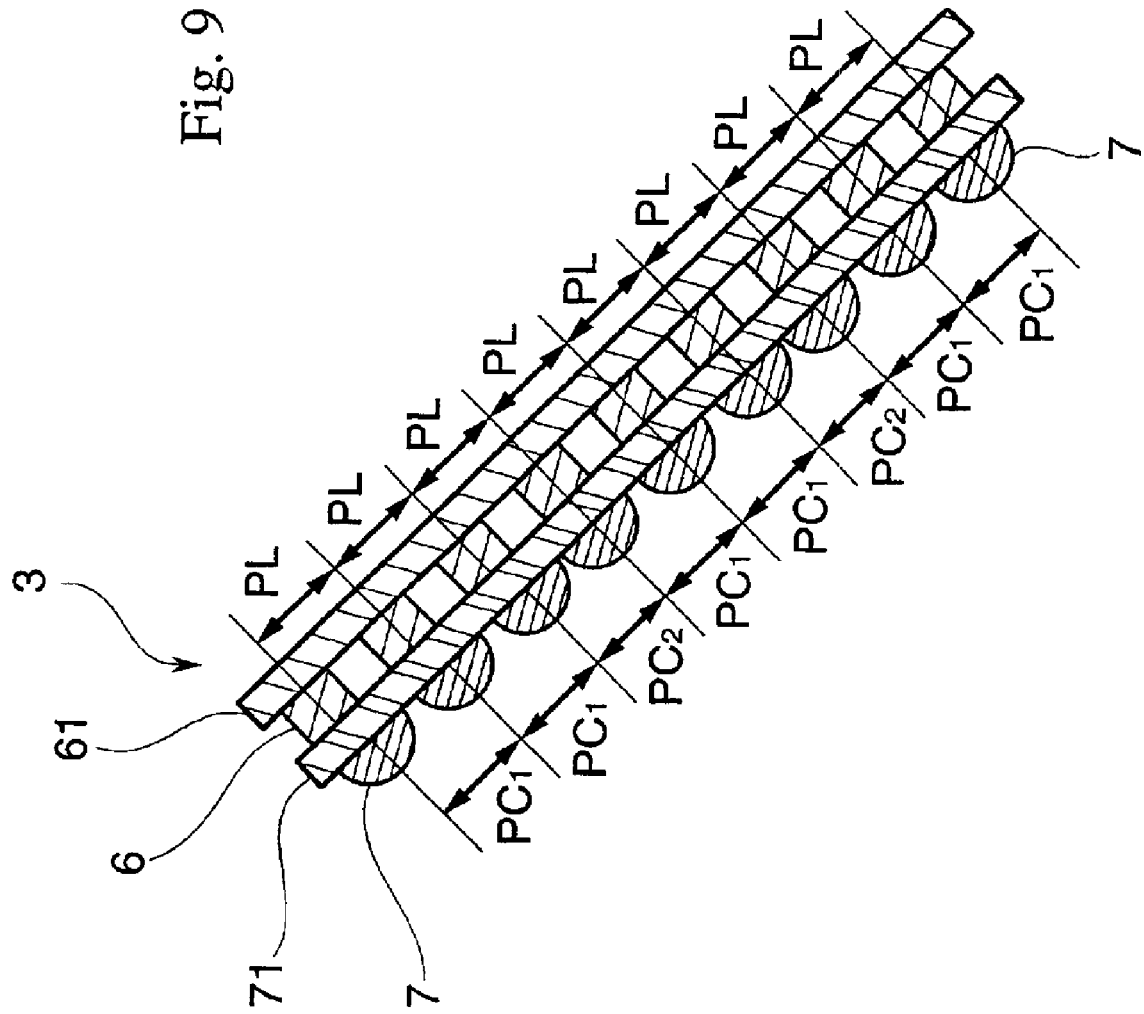
FIG. 9 is a detail view showing a partial structure of a lighting system for surface inspection in a variation of the present invention.
Figure 10:
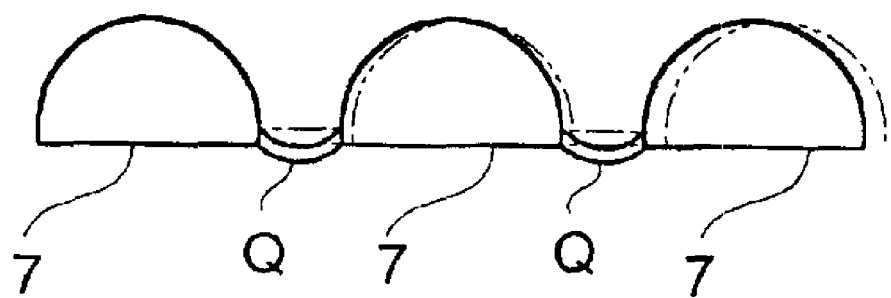
FIG. 10 is a detail view showing a partial structure of a lighting system for surface inspection in a variation of the present invention.
Figure 10:
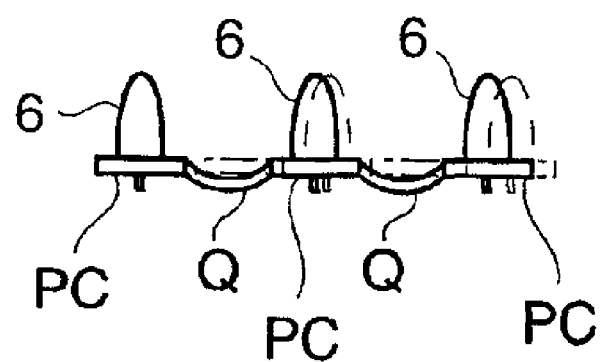

Though, in this embodiment, the aforementioned condition is met by adjusting the pitch PC of the cylindrical lenses 7 at the time of bonding them to the lens support plate 71 with the pitch PL between adjacent columns of LEDs 6 being kept constant, the condition may be met by reverse setting. Alternatively, it is possible to provide a pitch adjusting mechanism such as to make variable one of the pitch PL of LED columns and the pitch PC of the cylindrical lenses 7. Such an arrangement makes it possible to vary a light-concentrated area and a light-concentrating distance. Specifically, as shown in FIGS. 9 and 10, it is conceivable to interconnect adjacent cylindrical lenses 7 with flexible members Q or to mount columns of LEDs 6 respectively on corresponding printed boards PC interconnected through, for example, flexible members Q such as flexible boards.

A pair of such light-emitting members 3 thus constructed are disposed to form a flared shape widening toward the subject 2 for inspection in side view.

The half mirror 4 is of a rectangular plate shape and is disposed on an opposite side from the subject 2 about the light-emitting members 3 as inclined 45° to overlook the clearance S between the light-emitting members 3.

The second light-emitting member 5 is disposed forwardly (or rearwardly) of the half mirror 4 and comprises a plurality of LEDs 51 arranged in a line extending in the longitudinal direction, an LED support plate 52 supporting these LEDs 51, and a cylindrical lens 8 disposed on the half mirror 4 side of the line of LEDs 51. With this arrangement, light emitted from the LEDs 51 is concentrated through the cylindrical lens 8, then reflected by the half mirror 4 to pass through the clearance S, and concentrated onto a given surface region AR of the subject 2. The LED support plate 52 is mounted in the casing CS through a fixing mechanism 53 comprising an elongate hole extending in the subject feeding direction and a fastening screw so that the position thereof can be changed in the subject feeding direction thereby to vary the distance between the LEDs 51 and the cylindrical lens 8.

The lighting system 1 for surface inspection thus constructed is used as part of a line-type surface inspection unit in which an image pickup device such as a CCD camera (not shown) is disposed outside the through-window S1 and which is adapted to inspect the surface of the subject 2 through the through-window S1 and the clearance S by means of the image pickup device.

Accordingly, the lighting system 1 for surface inspection and the surface inspection unit thus constructed are capable of lighting a given surface region of subject 2 for inspection obliquely from an upper forward side and an upper rearward side by means of the pair of light-emitting members 3 and from just above through the half mirror 4 by means of the second light-emitting member 5 while, at the same time, making it possible to concentrate light emitted from the light-emitting members 3 onto the given surface region AR through the cylindrical lenses 7, whereby the lighting luminous intensity can be improved efficiently. Further, since there are provided plural columns of LEDs 6, correspondingly to which respective cylindrical lenses 7 are disposed, it is possible to use an inexpensive cylindrical lens having a small diameter for each of the cylindrical lenses 7 as well as to concentrate light by merely establishing a positional relation between each column of LEDs 6 and a corresponding one of the cylindrical lenses 7, whereby the downsizing of the system as a whole and the lowering of the price can be promoted with no heavy manufacturing burden.

According to this embodiment, in particular, the use of glass for the lens support plate 71 makes it possible to reduce the influence of warpage or distortion due to heat even if resin is used for the cylindrical lenses 7 to lower the price.

Further, the use of chip-type LEDs allows the mounting density to be improved rather than the use of shell-type LEDs thereby making it possible to provide an increased quantity of light without any necessity of doing so forcibly.

Second Embodiment

Hereinafter, a second embodiment of the present invention will be described with reference to FIGS. 5 to 8. It is to be noted that the following description uses like reference characters to denote like parts corresponding to those of the first embodiment.

Figure 5:
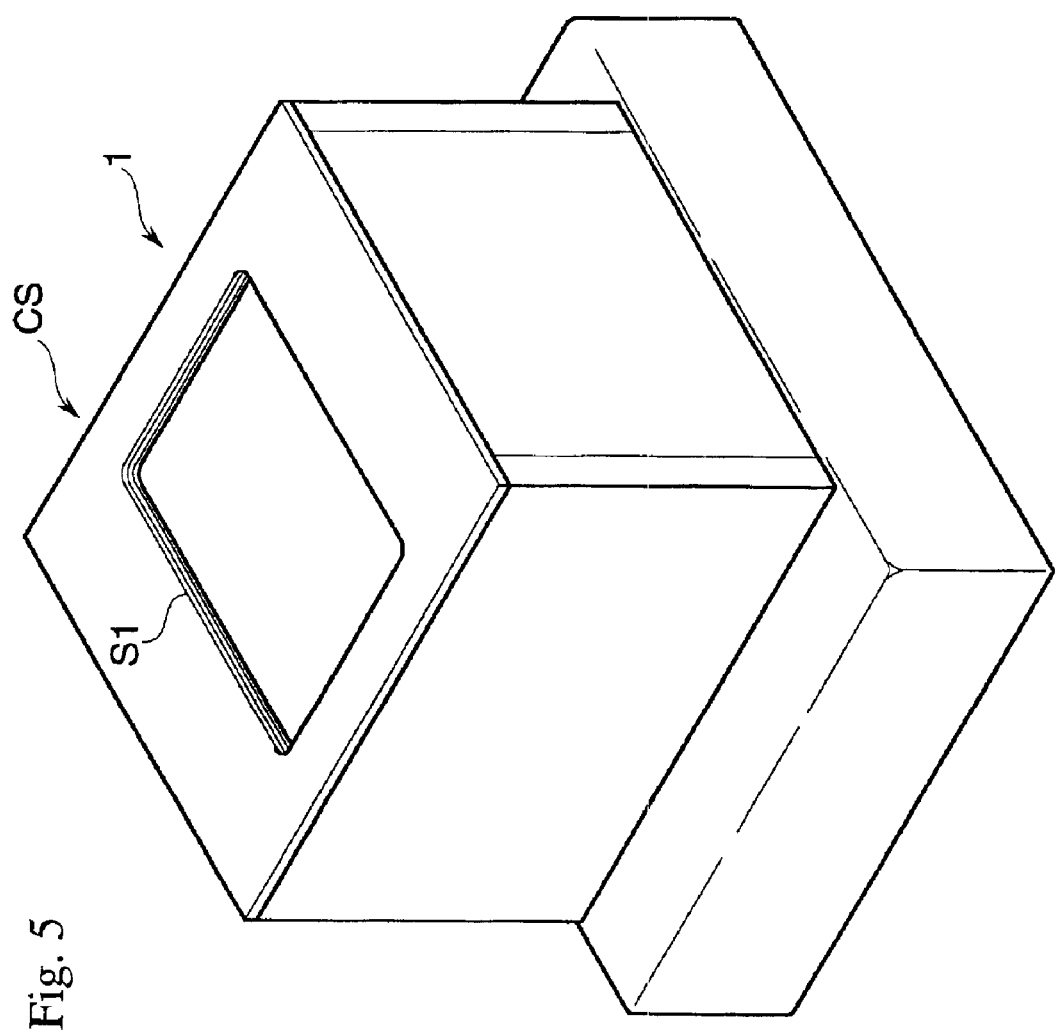
FIG. 5 is a general perspective view showing a lighting system for surface inspection in a second embodiment of the present invention.
Figure 6:
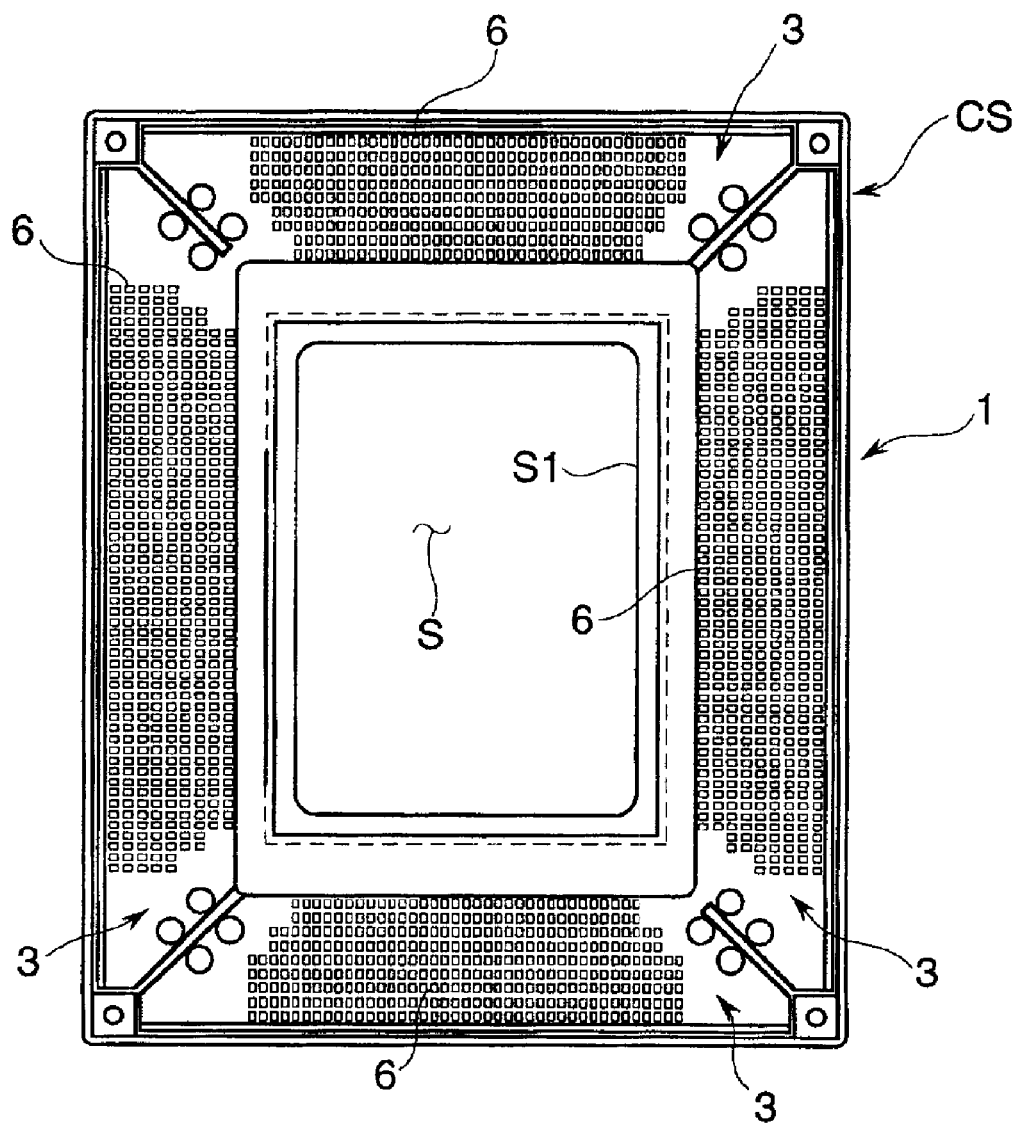
FIG. 6 is a bottom view of the lighting system for surface inspection in the same embodiment.
Figure 7:
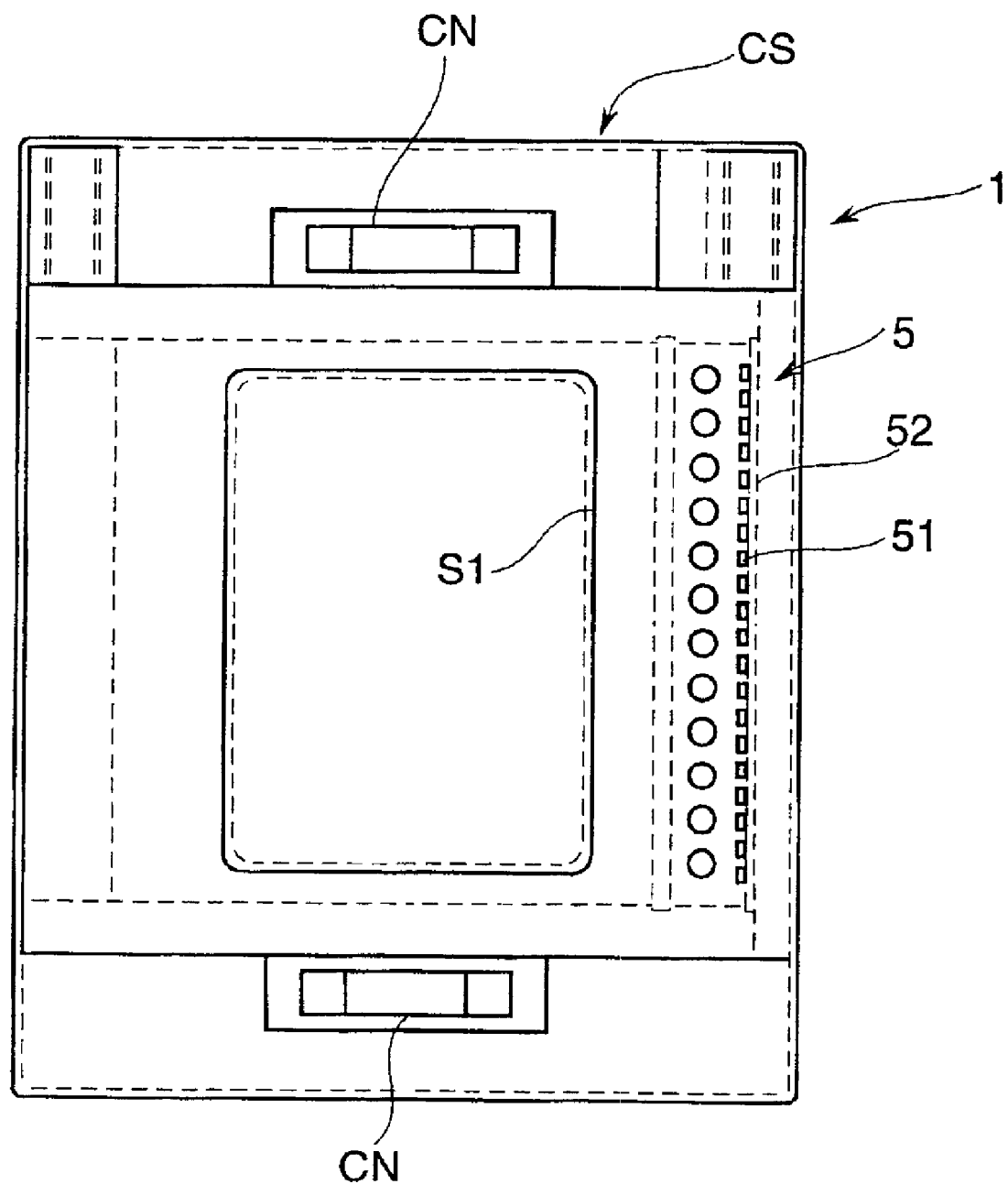
FIG. 7 is a side sectional view showing the internal structure of the lighting system for surface inspection in the same embodiment.

Like the lighting system 1 for surface inspection according to the first embodiment, lighting system 1A for surface inspection shown in FIGS. 5 to 7 is adapted for inspection of surface unevenness or the like of subject 2 for inspection (a printed board for example) and comprises a casing CS of a rectangular parallelepiped shape with its one side open, and light-emitting members 3 disposed within the casing CS.

The lighting system 1A for surface inspection according to this embodiment basically differs from that according to the first embodiment in that two pairs of light-emitting members 3 are disposed to form a truncated pyramid and that the second light-emitting member and the half mirror are not provided. Such differences in construction are provided because the lighting system 1A according to this embodiment is adapted for inspection on a plane basis, while in contrast the lighting system 1 according to the first embodiment is adapted for inspection on a line basis.

Figure 8:
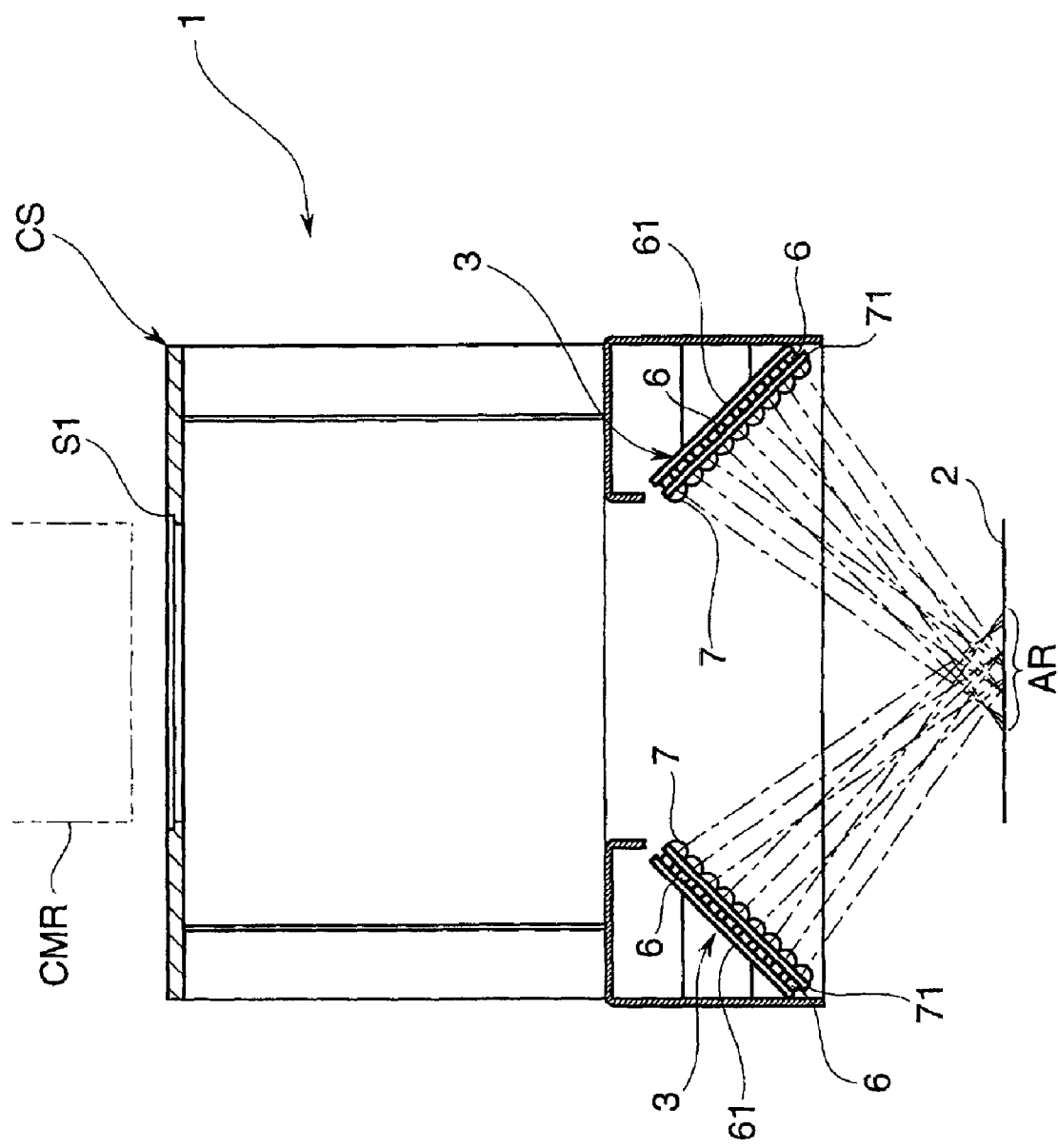
FIG. 8 is a detail view showing a partial structure of the lighting system for surface inspection in the same embodiment.

Referring specifically to the light-emitting members 3 particularly, as shown in FIG. 8, each of the light-emitting members 3 comprises nine columns of LEDs 6 and nine cylindrical lenses 7 disposed correspondingly to respective columns of LEDs 6 as in the first embodiment. Pitch PC between adjacent cylindrical lenses 7 is varied, with pitch PL between adjacent columns of LEDs 6 being kept constant. In this embodiment, pitch $PC_1$ between adjacent ones of three central cylindrical lenses 7 and between adjacent ones of three cylindrical lenses 7 located on each of opposite sides of the central cylindrical lenses is equal to pitch PL, while pitch $PC_2$ between adjacent ones of the cylindrical lens groups each comprising three such cylindrical lenses is smaller than pitch PL. Accordingly, a given surface region AR of the subject 2 to be illuminated has a slightly larger width than that in the first embodiment.

The lighting system 1A for surface inspection thus constructed is used as part of a surface inspection unit in which an image pickup device CMR such as a CCD camera is disposed outside the through-window S1 and which is adapted to inspect the surface of the subject 2 through the through-window S1 and the clearance S by means of the image pickup device CMR.

Third Embodiment

Figure 11:
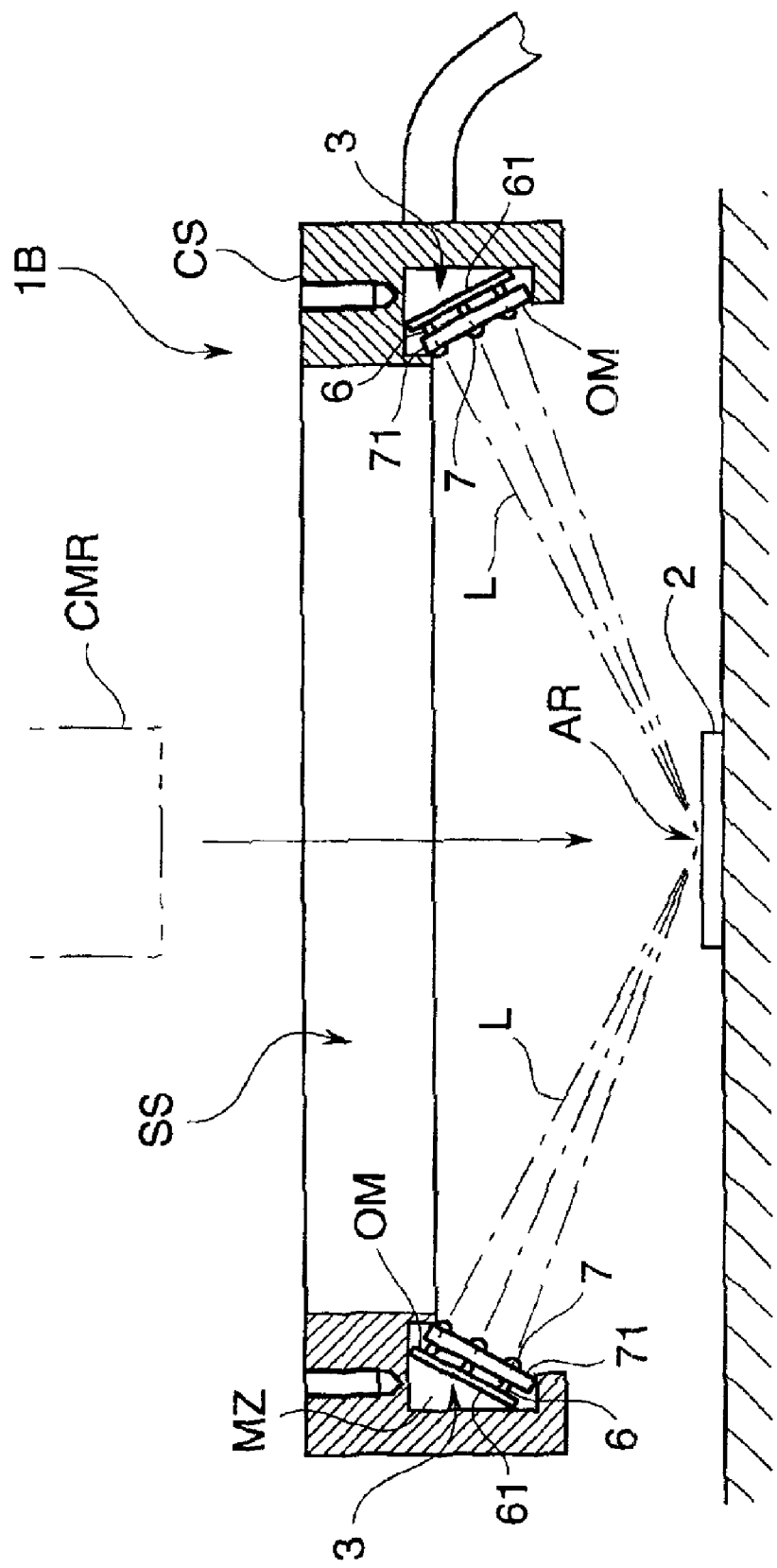
FIG. 11 is a vertical sectional view showing a lighting system for surface inspection in a third embodiment of the present invention.
Figure 12:
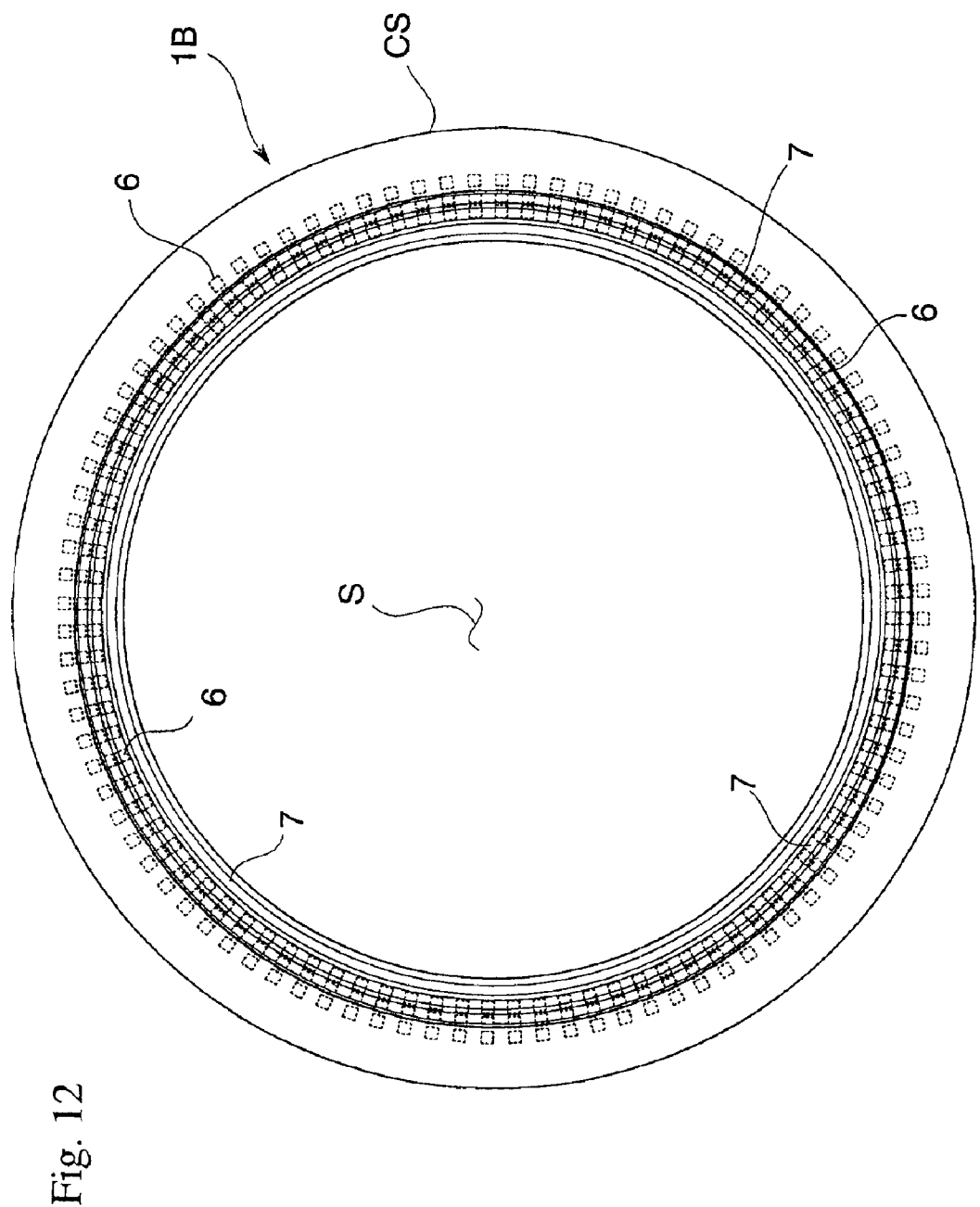
FIG. 12 is a bottom view of the lighting system for surface inspection in the same embodiment.
Figure 13:
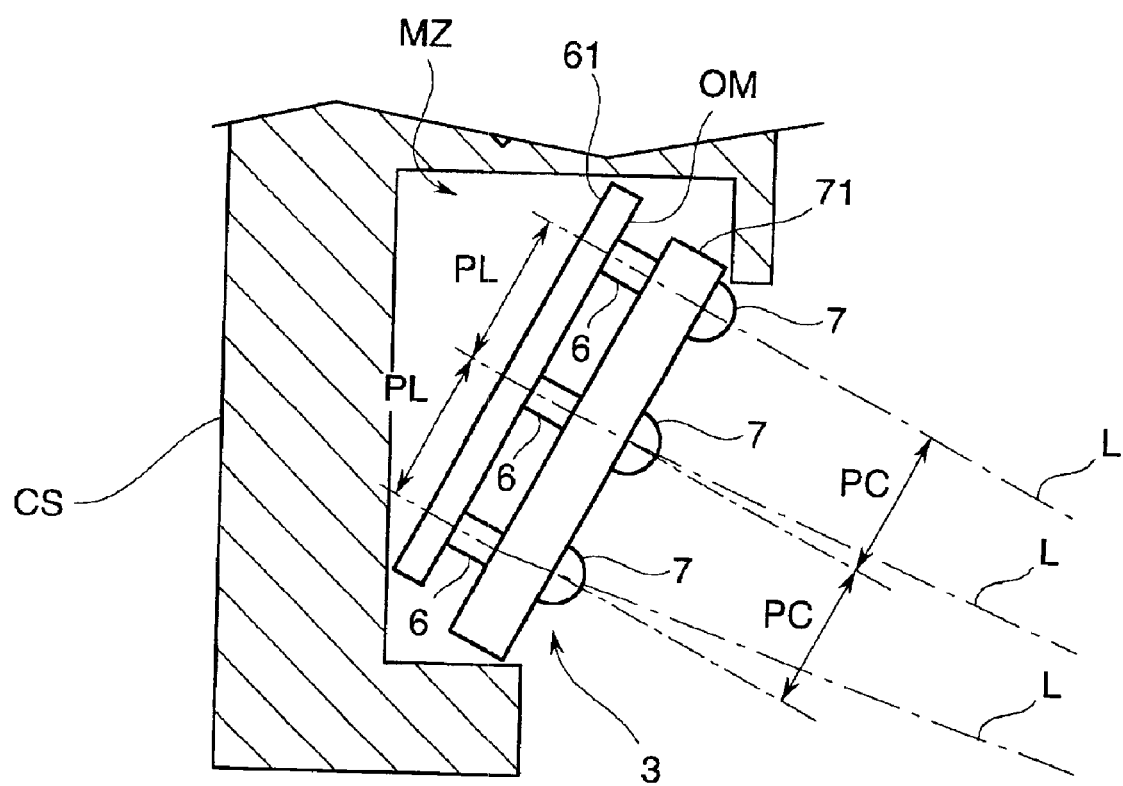
FIG. 13 is an enlarged fragmentary vertical sectional view of the lighting system for surface inspection in the same embodiment.

Hereinafter, a third embodiment of the present invention will be described with reference to FIGS. 11 to 13. It is to be noted that the following description uses like reference characters to denote like parts corresponding to those of the first embodiment.

Like the lighting system 1 for surface inspection according to the first embodiment, lighting system 1B for surface inspection shown in FIGS. 9 and 10 is adapted for inspection of surface unevenness or the like of subject 2 for inspection (a printed board for example) and comprises a casing CS, and a light-emitting member 3 disposed within the casing CS.

Referring specifically to each part, the casing CS is of a columnar shape with a central bore SS axially extending therethrough. The central bore SS has a lower internal surface formed with a circumferentially extending holding groove MZ holding the light-emitting member 3.

The light-emitting member 3 comprises an LED support plate 61, a plurality of LEDs 6 mounted on the LED support plate 61, a lens support plate 71, and a plurality of cylindrical lenses 7 mounted on the lens support plate 71.

The LED support plate 61 is a printed board defining a truncated conical concave surface OM, the printed board being formed by, for example, joining ends of flexible boards each forming a part of an annular shape. The posture of the lighting system 1B for surface inspection according to this embodiment is determined so that the truncated conical concave surface OM is oriented toward the subject 2 for inspection.

The LEDs 6 are of a chip type for example and are disposed on the truncated conical concave surface OM of the printed board 61. In this embodiment, the LEDs 6 are arranged in three lines forming concentric circles.

The lens support plate 71 is a transparent plate having an even thickness formed of an acrylic resin for example and is configured to form a truncated cone shape by molding or bending so that an outer surface 71a thereof extends along or adjacent the light-emitting surface of the LEDs 6.

The cylindrical lenses 7 are each shaped into a ring and formed of a transparent resin such as an acrylic resin. Three cylindrical lenses 7 corresponding to respective lines of LEDs are bonded to subject 2-facing side 71b of the lens support plate 71. The cylindrical lenses 7 and the lens support plate 71 may be formed separately from each other as described above or integrally with each other by molding or the like.

Like the first embodiment, pitch PC between adjacent cylindrical lenses is set smaller than pitch PL between adjacent LED lines so that lines L each linking the luminescence center of an LED belonging to each line to the center of a corresponding cylindrical lens 7 are concentrated toward a given region AR of the subject 2.

The lighting system 1B for surface inspection thus constructed is used as part of a surface inspection unit in which an image pickup device CMR such as a CCD camera is disposed outside the central bore SS and which is adapted to inspect the surface of the subject 2 through the central bore SS by means of the image pickup device CMR.

Other Embodiments

It should be noted that the present invention is not limited to the foregoing embodiments. It is needless to say that the posture of the foregoing surface inspection unit can be changed according to its applications; for example, the surface inspection unit may be used as inverted with its opening oriented upward. It is also possible to vary the number of columns or rows of LEDs mounted on each light-emitting member or to mold the cylindrical lenses integrally with the lens support plate. Further, it is possible to mount the second light-emitting member and the half mirror in the second embodiment. In this case, the second light-emitting member preferably comprises plural LEDs arranged lengthwise and crosswise to provide surface-emission of light.

INDUSTRIAL APPLICABILITY

As has been described in detail, the present invention is capable of concentrating light emitted from a light-emitting member onto a given surface region of a subject for inspection through cylindrical lenses and hence makes it possible to improve the lighting luminous intensity efficiently. Further, since there are provided plural columns of LEDs, correspondingly to which respective cylindrical lenses are disposed, it is possible to use an inexpensive cylindrical lens having a small diameter for each of the cylindrical lenses as well as to concentrate light by merely establishing a positional relation between each column of LEDs and a corresponding one of the cylindrical lenses, whereby the downsizing of the system and the lowering of the price can be promoted with no heavy manufacturing burden.

What is claimed is:

1. A lighting system for surface inspection comprising a pair of light-emitting members disposed to form a flared shape widening toward a subject for inspection in side view, the pair of light-emitting members each comprising a plurality of LEDs arranged lengthwise and crosswise on a side thereof facing the subject for inspection, and cylindrical lenses disposed correspondingly to respective columns of the LEDs, wherein the positional relation between each of the LED columns and a corresponding one of the cylindrical lenses is established such that light emitted from LEDs belonging to each LED column is concentrated onto a given surface region of the subject for inspection; wherein optical axes of light emitted from LEDs belonging to each LED column are parallel; and wherein pitch between adjacent cylindrical lenses is smaller than pitch between adjacent LED columns such that the light emitted from the LEDs belonging to each of the LED column is concentrated onto a given surface region of the subject for inspection.

2. The lighting system for surface inspection according to claim 1, further comprising a half mirror disposed on an opposite side from the subject for inspection about the pair of light-emitting members, and a second light-emitting member disposed on the opposite side from the subject for inspection about the light-emitting members such that light emitted from the second light-emitting member is reflected by the half mirror and then passes through a clearance defined between the pair of light-emitting members.

3. The lighting system for surface inspection according to claim 2, wherein the second light-emitting member comprises a plurality of LEDs arranged in a line, an LED support plate supporting the LEDs, and a cylindrical lens disposed on a side of the line of LEDs facing the half mirror.

4. The lighting system for surface inspection according to claim 3, wherein two pairs of light-emitting members are provided and arranged to form a truncated pyramid.

5. The lighting system for surface inspection according to claim 2, wherein the second light-emitting member comprises a plurality of LEDs arranged lengthwise and crosswise.

6. The lighting system for surface inspection according to claim 2, wherein the light-emitting members are each configured into an elongate rectangular shape extending along the LED columns.

7. The lighting system for surface inspection according to claim 2, which is provided with a pitch adjusting mechanism capable of varying at least one of a distance between adjacent ones of the LED columns and a distance between adjacent ones of the cylindrical lenses.

8. The lighting system for surface inspection according to claim 2, wherein two pairs of light-emitting members are provided and arranged to form a truncated pyramid.

9. A surface inspection unit utilizing a lighting system for surface inspection as recited in claim 2, comprising an image pickup device disposed on an opposite side from a subject for inspection about a half mirror for picking up an image of a surface of the subject illuminated by light-emitting members and a second light-emitting member through the half mirror and a clearance between the light-emitting members.

10. The lighting system for surface inspection according to claim 1, wherein the light-emitting members are each configured into an elongate rectangular shape extending along the LED columns.

11. The lighting system for surface inspection according to claim 10, which is provided with a pitch adjusting mechanism capable of varying at least one of a distance between adjacent ones of the LED columns and a distance between adjacent ones of the cylindrical lenses.

12. The lighting system for surface inspection according to claim 10, wherein two pairs of light-emitting members are provided and arranged to form a truncated pyramid.

13. A surface inspection unit utilizing a lighting system for surface inspection as recited in claim 10, comprising an image pickup device disposed on an opposite side from a subject for inspection about a half mirror for picking up an image of a surface of the subject illuminated by light-emitting members and a second light-emitting member through the half mirror and a clearance between the light-emitting members.

14. The lighting system for surface inspection according to claim 1, wherein two pairs of light-emitting members are provided and arranged to form a truncated pyramid.

15. A surface inspection unit utilizing a lighting system for surface inspection as recited in claim 14, comprising an image pickup device disposed on an opposite side from a subject for inspection about a half mirror for picking up an image of a surface of the subject illuminated by light-emitting members and a second light-emitting member through the half mirror and a clearance between the light-emitting members.

16. A surface inspection unit utilizing a lighting system for surface inspection as recited in claim 1, comprising an image pickup device disposed on an opposite side from a subject for inspection about a half mirror for picking up an image of a surface of the subject illuminated by light-emitting members and a second light-emitting member through the half mirror and a clearance between the light-emitting members.

17. A lighting system for surface inspection comprising a pair of light-emitting members disposed to form a flared shape widening toward a subject for inspection in side view, the pair of light-emitting members each comprising a plurality of LEDs arranged lengthwise and crosswise on a side thereof facing the subject for inspection, and cylindrical lenses disposed correspondingly to respective columns of the LEDs, wherein the positional relation between each of the LED columns and a corresponding one of the cylindrical lenses is established such that light emitted from LEDs belonging to each LED column is concentrated onto a given surface region of the subject for inspection; wherein the lighting system is provided with a pitch adjusting mechanism capable of varying at least one of a distance between adjacent ones of the LED columns and a distance between adjacent ones of the cylindrical lenses.

18. The lighting system for surface inspection according to claim 17, wherein two pairs of light-emitting members are provided and arranged to form a truncated pyramid.

19. A lighting system for surface inspection comprising plural lines of LEDs forming concentric circles on a truncated conical concave surface, and a plurality of cylindrical lenses concentrically disposed correspondingly to respective lines of LEDs, wherein the positional relation between each of the LED lines and a corresponding one of the cylindrical lenses is established such that light emitted from the LEDs is concentrated onto a given surface region: wherein plural lines of LEDs forming concentric circles are disposed on a truncated conical concave surfaces such that optical axes of light emitted from each of the LED lines are parallel; and wherein pitch between adjacent cylindrical lenses is smaller than pitch between adjacent LED lines such that the light emitted from each of the LED lines is concentrated onto a given surface region of the subject for inspection.

20. A surface inspection unit utilizing a lighting system for surface inspection as recited in claim 19, comprising an image pickup device disposed on an opposite side from a subject for inspection about a half mirror for picking up an image of a surface of the subject illuminated by light-emitting members and a second light-emitting member through the half mirror and a clearance between the light-emitting members.

* * * * *